United States Patent
Itsuji et al.

(10) Patent No.: US 7,922,659 B2
(45) Date of Patent: Apr. 12, 2011

(54) METHOD OF IDENTIFICATION OF LIVING BODY AND APPARATUS FOR IDENTIFICATION OF LIVING BODY

(75) Inventors: Takeaki Itsuji, Hiratsuka (JP); Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 504 days.

(21) Appl. No.: 10/570,770

(22) PCT Filed: Mar. 24, 2005

(86) PCT No.: PCT/JP2005/006225
§ 371 (c)(1), (2), (4) Date: Mar. 7, 2006

(87) PCT Pub. No.: WO2005/092191
PCT Pub. Date: Oct. 6, 2005

(65) Prior Publication Data
US 2007/0030115 A1    Feb. 8, 2007

(30) Foreign Application Priority Data
Mar. 26, 2004  (JP) ................... 2004-092398

(51) Int. Cl.
*A61B 5/117* (2006.01)
(52) U.S. Cl. .......................... 600/300; 342/22
(58) Field of Classification Search ............. 600/547, 600/407, 300, 409, 554; 607/51
See application file for complete search history.

(56) References Cited

U.S. PATENT DOCUMENTS

| | | | |
|---|---|---|---|
| 3,872,443 A | 3/1975 | Ott | |
| 6,336,045 B1 * | 1/2002 | Brooks | 600/547 |
| 6,343,140 B1 * | 1/2002 | Brooks | 382/115 |
| 6,367,695 B1 * | 4/2002 | Mair et al. | 235/380 |
| 6,747,736 B2 * | 6/2004 | Takahashi | 356/319 |
| 6,928,181 B2 * | 8/2005 | Brooks | 382/115 |
| 7,073,129 B1 * | 7/2006 | Robarts et al. | 715/740 |
| 7,135,980 B2 * | 11/2006 | Moore et al. | 340/573.1 |
| 7,248,995 B2 | 7/2007 | Itsuji et al. | |
| 2002/0031245 A1 * | 3/2002 | Rozenberg et al. | 382/125 |
| 2003/0072475 A1 * | 4/2003 | Tamori | 382/124 |

(Continued)

FOREIGN PATENT DOCUMENTS

DE       195 47 818 A1    6/1997

(Continued)

OTHER PUBLICATIONS

U.S. Appl. No. 11/632,958, filed Jan. 19, 2007, Inventor T. Ouchi.

(Continued)

*Primary Examiner* — Henry M Johnson, III
*Assistant Examiner* — Bobby Soriano
(74) *Attorney, Agent, or Firm* — Fitzpatrick, Cella, Harper & Scinto

(57) ABSTRACT

A method of identification of a living body is provided. The method comprises steps of detecting an electromagnetic wave in a frequency band ranging from 300 GHz to 30 THz transmitted from the living body, extracting plural kinds of information from the detected electromagnetic wave, and deriving therefrom information on the living body and information inherent to the living body, and comparing the information on the living body and the information inherent to the living body with preliminarily memorized information. This method identifies an individual living body with improved real-time detectableness and higher security to prevent illegal pretension.

11 Claims, 5 Drawing Sheets

U.S. PATENT DOCUMENTS

| | | |
|---|---|---|
| 2005/0046584 A1* | 3/2005 | Breed .................... 340/825.72 |
| 2005/0180620 A1* | 8/2005 | Takiguchi .................... 382/128 |
| 2006/0085160 A1 | 4/2006 | Ouchi |
| 2006/0197021 A1 | 9/2006 | Ouchi |
| 2006/0214176 A1 | 9/2006 | Ouchi et al. |
| 2006/0227340 A1 | 10/2006 | Shioda et al. |
| 2006/0244629 A1 | 11/2006 | Miyazaki et al. |
| 2007/0195921 A1 | 8/2007 | Ouchi |
| 2007/0215810 A1 | 9/2007 | Kurosaka et al. |
| 2007/0235718 A1 | 10/2007 | Kasai et al. |
| 2007/0252604 A1 | 11/2007 | Ouchi et al. |
| 2008/0146890 A1* | 6/2008 | LeBoeuf et al. ............. 600/300 |
| 2008/0146892 A1* | 6/2008 | LeBoeuf et al. ............. 600/300 |

FOREIGN PATENT DOCUMENTS

| | | |
|---|---|---|
| EP | 0 197 810 A1 | 10/1986 |
| EP | 197810 A1 * | 10/1986 |
| EP | 1 353 292 A1 | 10/2003 |
| FR | 0197810 A1 * | 3/1985 |
| JP | 2001-195364 A | 7/2001 |
| JP | 2002-236666 A | 8/2002 |

OTHER PUBLICATIONS

U.S. Appl. No. 10/587,262, filed Jul. 26, 2006, Inventor, T. Itsuji.

Office Action issued on Dec. 28, 2007 by the Chinese Patent Office.

R. M. Woodward, et al., "Terahertz pulse imaging in reflection geometry of human skin cancer and skin tissue", Physics in Medicine And Biology, vol. 47, 2002, pp. 3853-3863.

International Search Report and Written Opinion, mailed Jun. 29, 2005.

* cited by examiner

METHOD OF IDENTIFICATION OF LIVING BODY AND APPARATUS FOR IDENTIFICATION OF LIVING BODY

TECHNICAL FIELD

The present invention relates to a method of identification of a living body by utilizing biological information of the living body, and an apparatus therefor.

BACKGROUND ART

Investigations are being made on identification of living bodies including individual persons. Some methods and apparatuses for identification of an individual person conduct the identification by utilizing a physical feature of the individual person such as a fingerprint, a voiceprint, a voice, and a retina. Such an identification apparatus, which utilizes only a characteristic pattern of the specified feature of the person, has problems in security, since another person can obtain and imitate the pattern data. Actually, a second person can simply cut out the physical characteristic portion from a first person and can pretend to be the first person.

To cancel the above disadvantage, methods and apparatuses for identification of the individual person have been disclosed as shown below.

Japanese Patent Application Laid-Open No. 2001-195364 discloses combination of two or more identification systems such as retina identification, fingerprint identification, voice identification, and voiceprint identification to improve real-time responsiveness (quick identification of the objective person to be true) for security.

Japanese Patent Application Laid-Open No. 2002-236666 employs additional system for checking the quality of the biological information such as a fingerprint, a voiceprint, a face feature, and an iris to improve real-time detectableness in the identification for security. The information-quality-checking system is exemplified by a temperature sensor, a skin electroconductivity tester, and an image pickup apparatus for observation of movement of a mouth or an iris.

The method of using plural kinds of individual identification systems, like the method disclose in the above Japanese Patent application Laid-Open No. 2001-195364, requires combination of many individual identification systems for real-time individual identification. However, use of the plural identification systems necessarily makes larger the system constitution of the identification apparatus disadvantageously. Further, the use of the plural systems for individual identification can be ineffective if a second person imitates all the objective physical data of the individual identification apparatus. Thus, even if this method can increase the probability for the precise identification of an individual person, it is difficult to prevent completely the false pretension.

The method of additional use of an information-quality-checking system for securing the real-time responsiveness of the individual identification system, like the method of above Japanese Patent Application Laid-Open No. 2002-236666 can improve greatly the real-time responsiveness. However, the system is necessarily larger corresponding to the information-quality-checking system, disadvantageously.

Any of the above disclosures improves the real-time responsiveness to prevent pretension to be the subject person for higher security. However, for the real-time responsiveness, plural identification systems should be employed, or an information-checking system should be added, which enlarges the entire identification system. In particular, in recent years, mobile products such as a mobile phone have come to be widely used. The individual identification apparatus for reservation systems, cashing systems, and the like employing the mobile product are naturally demanded to be smaller in size.

DISCLOSURE OF THE INVENTION

For solving the above problems, the present invention provides a method of individual person identification and an apparatus therefor constituted as shown below.

According to an aspect of the present invention, there is provided a method of identification of a living body, comprising the steps of:
detecting an electromagnetic wave in a frequency band ranging from 300 GHz to 30 THz transmitted from the living body;
extracting plural kinds of information from the detected electromagnetic wave derive therefrom information on the living body and information inherent to the living body; and
comparing the information on the living body and the information inherent to the living body with preliminarily memorized information.

The information on a living body is preferably any one selected from the group consisting of information on movement of the living body and information on a property of a material comprised of the living body.

The information on movement of the living body is preferably any one selected from the group consisting of pulse vibration, voice cord variation, bone vibration, shape change of eye lens, pupil contraction and pupil dilation.

The information on a property of a material comprised of the living body is preferably any one selected from the group consisting of a temperature of the living body, absorption of the electromagnetic wave by the living body, reflection of the electromagnetic wave by the living body, an impedance of the living tissue, a dielectric constant of a tissue of the living body, DNA, and a water content of a tissue of the living body.

The information inherent to the living body is preferably any one selected from the group consisting of a fingerprint, a voiceprint and a retina pattern.

The step of detecting an electromagnetic wave is preferably comprised of the step of projecting an electromagnetic pulse wave to the living body to detect a reflected wave of the electromagnetic wave.

According to another aspect of the present invention, there is provided an apparatus for identifying a living body, comprising:
a detecting section for detecting an electromagnetic wave in a frequency band ranging from 300 GHz to 30 THz transmitted from the living body;
an information-collecting section for extracting plural kinds of information from the detected electromagnetic wave to derive therefrom information on the living body and information inherent to the living body; and
an identifying section for comparing the information on the living body and the information inherent to the living body with preliminarily memorized information to identify the living body.

According to the present invention, from electric wave transmitted from a living body, plural kinds of information are derived, and the individual person is identified by combination of the plural kinds of information. Thereby plural systems need not be employed for detection of the information of the living body, which simplifies the identification apparatus constitution effectively.

BEST MODE FOR CARRYING OUT THE INVENTION

Figure 1:
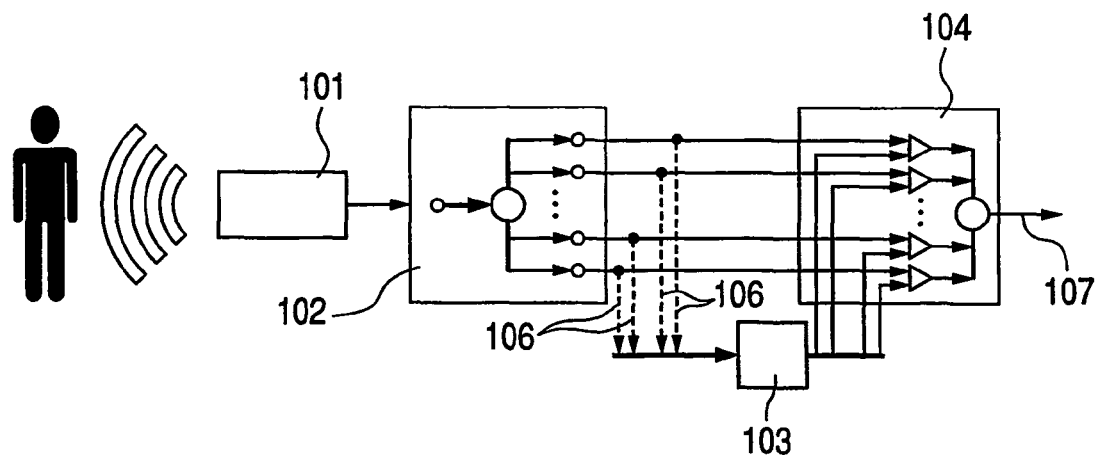
FIG. 1 is a drawing for explaining the constitution of the identification apparatus of the present invention.

Embodiments of the present invention are explained below by reference to drawings. In the description, the reference symbols are the same as the ones in the drawings.

FIG. 1 is a block diagram of the identification apparatus of the present invention. The identification apparatus of the present invention is constituted of electromagnetic wave-detecting section 101, biological information-collecting section 102, biological information-memorizing section 103, and identifying section 104:

the electromagnetic wave-detecting section 101 detects electromagnetic wave transmitted from a living body;

the biological information-collecting section 102 extracts plural kinds of information from the electromagnetic signals detected by electromagnetic wave-detecting section 101, and collects information on the living body and information inherent to the living body from the extracted plural kinds of information;

the biological information-memorizing section 103 memorizes reference information necessary for identification of the living body from the information (information of the living body and information inherent to the living body) collected by biological information-collecting section 102; and the identifying section 104 compares the respective kinds of information collected by the biological information collecting section with the reference information memorized in biological information-memorizing section 103, thereby judges whether or not the living body is the objective living body, and outputs (107) the judgment result as the identification result.

In the present invention, an electromagnetic wave is employed as the means for sensing the biological information. This electromagnetic wave is a pulsed or continuous electromagnetic wave of any frequency in a frequency range from 300 GHz to 30 THz (hereinafter referred to as a "terahertz wave"). The terahertz wave has properties of the electromagnetic wave: rectilinear propagation and some penetrativeness through an article. Such properties are applicable widely in various technical fields: measurement of a position of an article through an obstacle (an inorganic material) with accuracy of an order of tens of micrometers from phase delay by an obstruction like a radar; image formation by utilizing spectral information or absorption/reflection properties; and like application fields.

By an analogous technique, an article can be sensed through an obstruction by a millimeter wave. However, with this technique, the article cannot be identified through the obstruction even though the presence of the article can be detected, since the millimeter wave cannot be focused sharply owing to the long wavelength of this electromagnetic wave in comparison with the terahertz wave. For example, in detection of a human body caught under tiles and rocks, the millimeter wave can detect the presence of a thing like a living body different from the tiles and rocks, but cannot obtain the information whether the living body is human body, whether the living body is breathing, or in what state the living body is buried.

The frequency region of the terahertz covers absorption wavelengths of many biological molecules of proteins or the like. Therefore the terahertz wave can be useful characteristically in various application fields such as sensing of a non-labeled biological molecule, and imaging of a biological molecule by difference in a propagation state of the terahertz wave. In the above-mentioned example of detection of a human body under the tiles and rocks, sensing of the biological molecules may give information on the name of the person or the health state of the person, not only the state of the human body. Therefore the technique employing the terahertz is obviously different from the technique employing the millimeter wave.

Generally an article is known to radiate an electromagnetic wave depending on the temperature T thereof according to the Planck's equation below.

$$Bv(T) = \frac{\frac{2hv^3}{c^2}}{\exp\left(\frac{hv}{kT}\right) - 1}$$

where $B_v(T)$: spectral radiance; h: Planck constant, v: frequency; c: light velocity; k: Boltzmann constant, T: absolute temperature of an article. Therefore, a passive type system can be constituted with measurement of electromagnetic spectra depending on the absolute temperature an article.

Electromagnetic wave-detecting section 101 is constituted of a part for generating/irradiating a pulsed or continuous terahertz wave and a part for detecting a terahertz wave containing superposed biological information. The terahertz wave-generating/irradiating part may be a frequency conversion system which converts ultrashort pulse signals into a pulse wave within the aforementioned electromagnetic frequency band width by a light transmission element or the like. However, in the individual person-identifying apparatus of the present invention, the terahertz wave-generating/irradiating part is not limited thereto provided the part is capable of generating the above-mentioned terahertz wave in a pulse shape or a continuous wave shape. The terahertz wave-generating/irradiating part may be constituted to vary the directivity of the terahertz wave to conduct sensing in an intended range. In this constitution, the sensing mechanism may be a mechanical constitution with an actuator, or may be a constitution in which an antenna is provided in the terahertz generating/irradiating part and the directivity of the antenna is made variable, but the constitution is not limited thereto, insofar as the part is capable of sensing a living body with the terahertz wave. The other part of the electromagnetic wave-detecting section, namely a terahertz wave-detecting part for detecting a terahertz wave containing superposed biological information, may be a system employing a light transmission element, or a system employing an electromagnetic wave detecting element like a bolometer, but is not limited thereto. Besides the constitution which projects a terahertz wave to a living body and detects a change of the terahertz wave transmission state by the reflected wave as described above, the electromagnetic wave-detecting section 101 may have a constitution in which a terahertz wave emitted from a living body is detected, or terahertz-generating element is provided in the living body side and the terahertz wave from the element is detected.

Biological information-collecting section 102 collects plural kinds of biological information detected by electromagnetic wave-detecting section 101 (information on the living body and information inherent to the living body) for identification by isolation and extraction from the terahertz wave carrying the information in superposition.

In the present invention, the information extracted from the electromagnetic wave transmitted from a living body includes a phase change. The phase change can be used for detection of position information showing movement of the living body. For example, for obtaining human voice information, phase information is firstly collected from electromagnetic wave information inputted to biological information-collecting section 102 by a phase detecting circuit, and frequency of the voice is detected from the periodicity of the phase information. Then a signal in the voice signal frequency band is extracted by use of a filter or the like to obtain biological information of bone vibration caused by voice sound transmitting through a human body. Otherwise information on biological information such as breathing and pulse can be obtained by extracting a relatively regular vibration component such as a vertical movement of a breast, and a vibration component of a skin surface. Besides the inherent vibration of the human body, movement of a muscle or bone joint of a human body can be extracted by detecting a terahertz wave at a fixed detection site (a fixed point or a region on a human body) and plotting the phase displacement at the detection site in time series. Other than the biological information on the movement of living body, information inherent to a living body (a pattern inherent to the living body) can be obtained by sensing a part of the living body (specifically a human body). For example, a voiceprint or a fingerprint can be collected as the inherent characteristic pattern. In the aforementioned detection of a voice sound, a voiceprint can be obtained as the information inherent to the living body by extracting a vibration as a phase change of the terahertz wave at the site where vocalization vibration can be detected (a bone rising portion) and calculating frequency spectrum for the respective generated sounds. Otherwise a characteristic pattern (a pattern inherent to a living body) on a skin surface like a finger print can be extracted by focusing a terahertz wave on a finger tip, allowing the focus point to scan successively, detecting slight impression at the fingertip from the phase change at the scanned points, and reconstructing the impression information. Since the position information given by the terahertz wave depends on properties of the living body, a living body can be identified by this phase change.

The terahertz wave transmitted from the living body gives phase information and amplitude information, both varying with the properties of the living body. Therefore, the change of amplitude information, or changes of amplitude information and phase information from the terahertz wave are utilizable for detection of biological information (information on the living body, or information inherent to the living body) For example, in sensing a region of a living body, the difference of the substances constituting the living body can be observed through steps: extraction of the amplitude of the electromagnetic wave as information by use of a peak detecting circuit, from electromagnetic wave information inputted to biological information-collecting section 102; estimation of the quantity of terahertz absorption by the living body or the quantity of terahertz reflection by the living body as the biological information; and comparison of the derived information with the memorized information. As another example, the living tissue such as protein constituting the part of the human body can be specified from the aforementioned information on the phase change or amplitude change of the terahertz wave through steps: estimation of characteristics such as a dielectric constant or impedance of the living body to obtain information inherent to the living body; and comparison of the obtained information inherent to the living body with the memorized information. For example, a pattern characteristic to a human body such as a blood vessel pattern on a retina can be obtained from the difference of a biological tissue constituting the living body. Further, DNA information characteristic to an individual person can be obtained. Information on movement of a living body can be obtained by monitoring a time-series change of material property at a fixed point of the living body (e.g., pupil contraction caused by local movement of a living body). Other than the specification of a living tissue, this method is useful for proof of the identified object to be a living body by plotting changes of the detected quantity for local change of the identification conditions (humidity, temperature, etc.) since the detected quantity depend on the water content and the temperature conditions.

Several kinds of biological information are mentioned which can be derived from a terahertz wave obtained from electromagnetic wave-detecting section 101. However, the information is not limited thereto. The means for obtaining the biological information is explained above by reference to using several circuit constitutions, but the constitution is not limited thereto. For example, an arithmetic processing means may be employed for deriving plural kinds of biological information without employing a circuit element.

Biological information-memorizing section 103 memorizes reference information corresponding to the biological information obtained by biological information-collecting section 102. The reference information on the living body to be identified should be entered preliminarily. In the present invention, the entry of the reference information on the living body into biological information-memorizing section 103 is conducted, for example, by system in which electromagnetic wave-detecting section 101 senses a living body to obtain necessary biological information and this biological information is memorized (106) in biological information-memorizing section 103, but is not limited thereto. The biological information-memorizing section 103 may be made detachable from the individual person identification apparatus. Biological information-memorizing section 103, when detached, serves as a key like an ID card, providing a security means for more safe system. With such biological information-memorizing section 103 as a key function, plural individual person identification apparatuses can be used commonly.

Identifying section 104 compares plural kinds of the biological information from biological information-collecting section 102 with the respective reference information of the living body memorized in biological information-memorizing section 103, and from the correlation, judges whether the living body to be identified is entered living body or not, and outputs the result of the identification. More specifically, in addition to the characteristic pattern inherent to an individual person, additional biological information (e.g., information on the movement of the living tissue, and information on the material of the living tissue) is employed to improve the real-time detectableness and precision of the identification. In the comparison operation, all of the derived plural kinds of information may be utilized, or combination of the plural kinds of information may be changed at random in every identification operation for higher real-time detectableness and higher precision of the identification. The change of the combination of the biological information introduced to the identification apparatus in every identification operation improves the safety of the system.

The operation of the identification apparatus of the present invention is described below.

The identification apparatus of the present invention identifies an individual person through the steps below.

(Entry of Biological Information)

(1) A terahertz wave from a living body is detected.

(2) From the detected terahertz wave, necessary kinds of information are extracted and are memorized in a recording medium.

(Identification)

(1) The memorizing medium having memorized biological information is connected to the identification apparatus. (This step is omitted when the identification apparatus and the memorizing medium are integrated.)

(2) A terahertz wave is detected from the site having biological information required by the identification apparatus.

(3) From the detected terahertz wave, plural kinds of information required by the identification apparatus are extracted and collected. (Preferably collected are a characteristic pattern inherent to the living body and biological information for improving the real-time detectableness of the characteristic pattern.)

(4) The respective derived pieces of biological information are compared with the reference information memorized in the memory medium, and the living body is identified by the correlation.

The identification by use of plural kinds of biological information as above will ensure the real-time detectableness of the identification and will improve the safety of the system.

EXAMPLES

Example 1

Voiceprint Identification

This Example shows an application of an identification apparatus of the present invention to identification of an individual person by combination of plural kinds of organ movement information. A voiceprint identification apparatus is used in this Example. The voiceprint identifying apparatus can render unnecessary an ID card or password which is essential in log-in to an ATM, a personal computer, or the like.

Figure 2A:
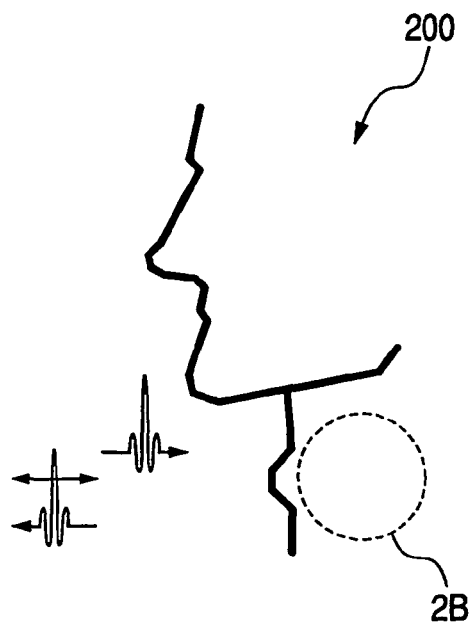
FIGS. 2A and 2B are drawings for explaining the voice-print identification apparatus of Example 1.
Figure 2B:
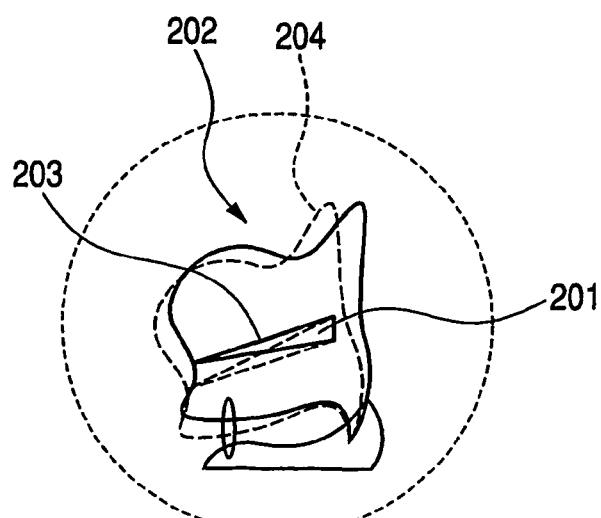

The voiceprint identification apparatus in this Example has a constitution as shown in FIG. 1. An impulse wave of a pulse width of about 10 psec is employed as the electromagnetic wave. As the biological information, this Example utilizes vibration 203 of vocal cord 201 of human body 200 and movement 204 of larynx 202 in vocalization as shown in FIGS. 2A and 2B. A person makes a voice by vibrating vocal cord 201. For changing the vocalization state, vocal cord 201 is stretched or shortened by movement of larynx 202 up and down or tilting the larynx forward and backward by muscular tissues around larynx 202 as shown in FIGS. 2A and 2B.

In this example, the terahertz wave projected from electromagnetic wave-detecting section 101 is reflected by a portion of larynx 202 back to electromagnetic wave-detecting section 101. The reflected terahertz wave detected by electromagnetic wave-detecting section 101 contains, in superposition, information on vibration A of voice cord 201 transmitting through larynx 202 and information on distance variation caused by movement B of larynx 202 as a delay time of the terahertz wave introduced to electromagnetic wave-detecting section 101. By monitoring the delay time in time series, the distance relation between electromagnetic wave-detecting section 101 and larynx 202 can be derived according to the relation to the electromagnetic wave velocity:

$$\Delta t = (2\Delta d)/c$$

where $\Delta t$: delay time, $\Delta d$: positional variation, c: light velocity.

Figure 3A:
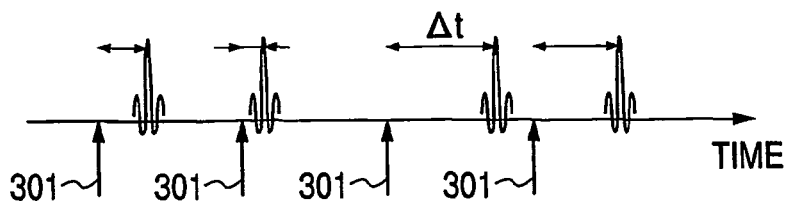
FIGS. 3A, 3B, 3C, 3D and 3E are drawings for explaining the operation in Example 1.
Figure 3B:
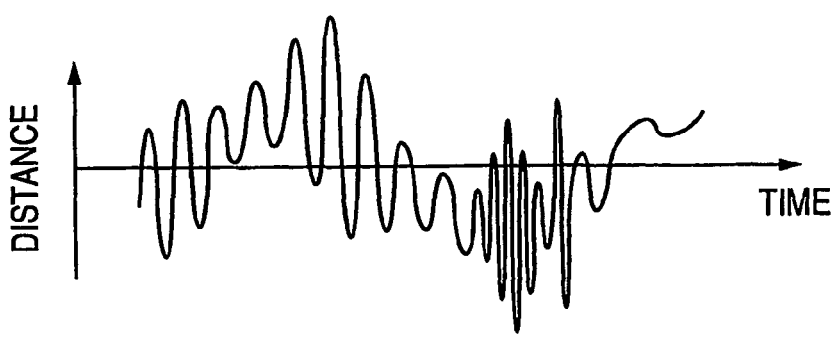

In this Example, the electromagnetic wave-detecting section 101 projects a terahertz wave to a portion of human larynx 202 at a constant time interval. The phase of the terahertz reflected by larynx 202 varies in correspondence with the position of larynx 202 and the vibration of voice cord 201. Biological information-collecting section 102 conducts sampling at regular intervals as the terahertz wave projection intervals of electromagnetic wave-detecting section 101. As described above, the phase of the terahertz is reflected by larynx 202 depends on the state of larynx 202. Therefore, the delay time $\Delta t$ of the terahertz wave varies for each sampling as shown in FIG. 3A (the sampling points being shown by arrows 301). From the dependency of the delay time $\Delta t$ on the distance between electromagnetic wave-detecting section 101 and larynx 202 in time series, a vibration waveform synthesized from vibration A of voice cord 201 by vocalization and movement B of larynx 202 can be detected as shown in FIG. 3B. For this detection, the sampling frequency (i.e., the interval of terahertz wave projection) should be sufficiently smaller than vibration A of voice cord 201.

Figure 3C:
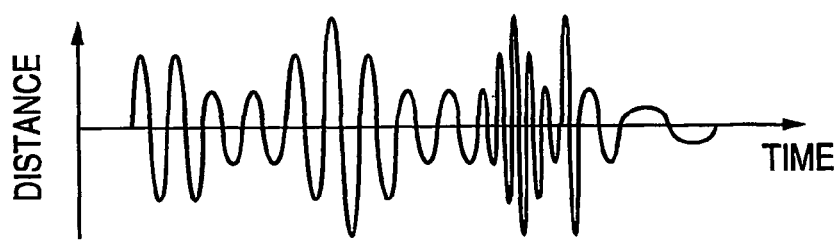
Figure 3D:
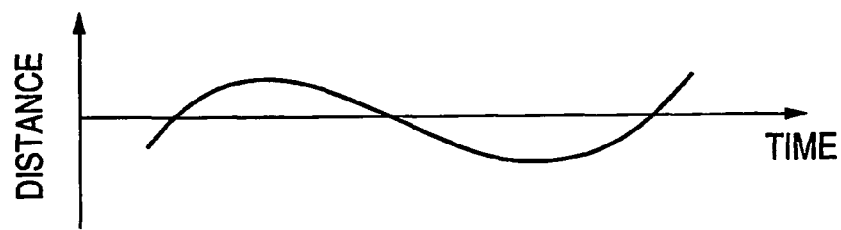
Figure 3E:
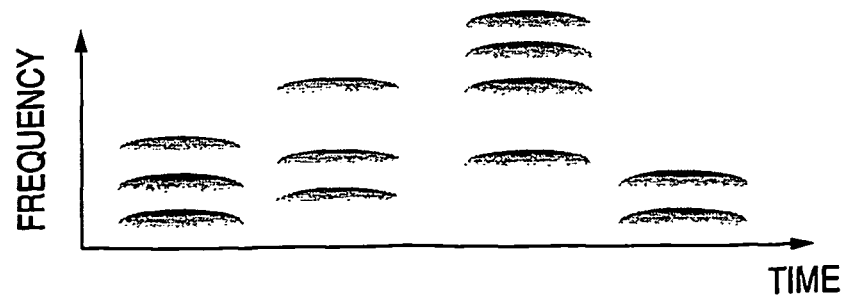

As described above, the vibration waveform derived from the distance relation between a portion of larynx 202 and electromagnetic wave-detecting section 101 is considered to be formed by superposition of the information on vibration of voice cord 201 caused by vocalization and the information on movement of larynx 202 for adjusting the vibration state of voice cord 201. Generally the information on the vibration of voice cord 201 and the information on movement of larynx 202 for adjusting the vibration state of voice cord 201 are different greatly in the frequency characteristics. Therefore, the two kinds of information can readily be separated by filtering or a like arithmetic processing. For example, by filtering the above vibration waveform for human voice frequency band, a vibration waveform of voice cord 201 can be derived which varies in vibration frequency in time series as shown in FIG. 3C. Biological information-collecting section 102 converts the time waveform of vibration A of voice cord 201 as shown in FIG. 3C into a time-series frequency spectrum as shown in FIG. 3E, and outputs it to identifying section 104 as voiceprint information on the voice of the person. On the other hand, the vibration waveform shown in FIG. 3B, which results from synthesis of the voice cord vibration and the larynx movement, is treated for extraction of the signal component in a low frequency region to detect movement of larynx 202 caused by vocalization of the person as shown in FIG. 3D. This information of movement B of larynx 202 is also introduced to identifying section 104.

In this Example, as described above, voiceprint information is derived as a characteristic pattern inherent to a living body, and the information on larynx movement in vocalization is also derived from the electromagnetic information detected by electromagnetic wave-detecting section 101 for improving the real-time detectableness of voiceprint information.

The process of this Example comprises a step of converting the voice of a person to voiceprint information in time series. Thereby from the voiceprint information obtained as shown in FIG. 3E, the voice of the person can be reproduced by converting the voiceprint information to voice cord vibration information as shown in FIG. 3C.

Identifying section 104 identifies the person by comparing the derived biological information with the reference signal memorized in biological information-memorizing section 103.

In this Example, the voiceprint and larynx movement of a living body are utilized in combination as the plural kinds of biological information, but the combination is not limited thereto. The information for the combination includes voice information before conversion to the voiceprint; voice information for a specified keyword; voiceprint information for a specified keyword; temperature information, an impedance change, a water content, and a skin thickness around the voice cord; voice tissue information. The number of the kinds of combined biological information is not limited to two.

As shown in this Example, combined use of the larynx movement information in a voiceprint identification apparatus improves real-time detectableness in the identification, thereby preventing effectively pretension to be the subject person, being different from a conventional method such as simple voiceprint recording. This method will improve the security in the identification.

The method of this Example derives voice information of a person from the vibration of a voice cord transmitted from a larynx. Therefore, the identification can be conducted precisely under noisy conditions without detecting an external signal noise component.

Example 2

Fingerprint Identification

This Example shows an application of an identification apparatus of the present invention to identification of an individual person by utilizing a combination of personal characteristic pattern with organ movement information. A fingerprint identification apparatus is employed in this Example. The fingerprint identification apparatus can render unnecessary the ID card or password which is essential in log-in to an ATM, a personal computer, or the like.

Figure 4:
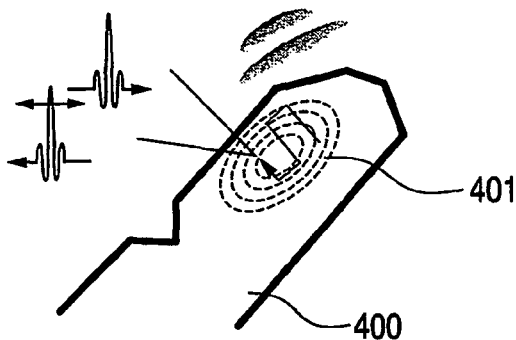
FIG. 4 is a drawing for explaining the fingerprint identification apparatus of Example 2.

The fingerprint identification apparatus in this Example has a constitution as shown in FIG. 1. An impulse wave of a pulse width of about 10 psec is employed as the electromagnetic wave. The biological information utilized in this Example is combination of fingerprint pattern on the fingertip and vibration of the pulse transmitted to the fingertip as shown in FIG. 4.

In this example, the terahertz wave is projected from electromagnetic wave-detecting section 101 to a fingertip portion of a human body and is reflected to electromagnetic wave-detecting section 101. The projected terahertz wave is focused on a fine portion in the region of the fingerprint pattern on a fingertip, and focused spot is allowed to scan successively the region of the finger print. Incidentally, the method of scanning of the fingertip is not limited thereto. Otherwise a part or the entire of the fingerprint region may be collectively scanned with electromagnetic wave-detecting sections 101 provided in plurality, or the fingertip is moved for scanning with the focused spot. The reflected terahertz wave detected by electromagnetic wave-detecting section 101 contains information on the shape of the fingerprint pattern A and information on the distance of electromagnetic wave-detecting section 101 as the delay of time of the electromagnetic wave for reaching the electromagnetic wave-detecting section 101. Therefore, from the delay time at the fingertip, the distance relation between electromagnetic wave-detecting section 101 and fingertip can be derived according to the relation with the electromagnetic wave velocity:

$$\Delta t = (2\Delta d)/c$$

where $\Delta t$: delay time, $\Delta d$: positional variation, c: light velocity.

In this example, electromagnetic wave-detecting section 101 focuses the terahertz wave on the fingertip, allows the focused spot to scan the region of the fingerprint pattern successively, and outputs the distance relation between the fingertip and electromagnetic wave-detecting section 101 at the scanning points to biological information-collecting section 102. The use of the terahertz wave enables measurement of the distance between the fingertip and electromagnetic wave-detecting section 101 with accuracy of micrometers. Therefore, the information on the delay of the terahertz wave transmitted from electromagnetic wave-detecting section 101 to biological information-collecting section 102 contains information on the fingerprint impression Further, since the surface of the fingertip is vibrated up and down slightly by pulse of the blood vessel, the terahertz wave delay information transmitted to biological information-collecting section 102 contains information on pulse vibration in addition of the fingerprint impression information.

Figure 5A:
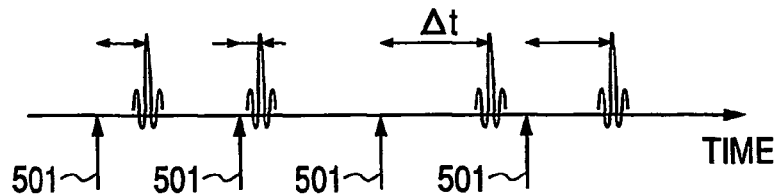
FIGS. 5A, 5B, 5C, and 5D are drawings for explaining the operation in Example 2.
Figure 5B:
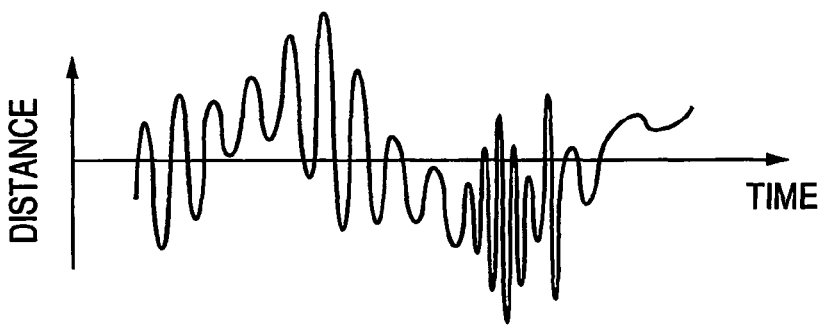

In this Example, the electromagnetic wave-detecting section 101 projects a terahertz wave to a fingertip portion of human body 400 at a constant time interval. The phase of the terahertz reflected from scanning points on the fingertip varies in correspondence with the fingerprint impression pattern and vibration of the fingertip by the pulse. Biological information-collecting section 102 conducts sampling at the same intervals as the terahertz wave projection intervals of electromagnetic wave-detecting section 101. As described above, since the phase of the terahertz wave reflected by the fingertip depends on the fingertip impression pattern and the pulse vibration state, the delay time $\Delta t$ of the terahertz wave varies for each sampling as shown in FIG. 5A (the sampling points being shown by arrows 501). By obtaining the relation of the terahertz wave delay $\Delta t$ with the distance between electromagnetic wave-detecting section 101 and the fingertip in time series, synthesized vibration waveform of the fingerprint pattern 401 (rise-depression of the fingerprint pattern crossing the scanning line of the focused terahertz wave) and the vibration waveform of pulse at the fingertip can be detected as shown in FIG. 5B. The vibration frequency of the vibration waveform (signal of the high frequency component in FIG. 5B) corresponding to the fingerprint pattern 401 is controlled by scanning frequency with the focused spots of the terahertz wave. The sampling frequency (i.e., the interval of terahertz wave projection) should be sufficiently smaller than the frequency derived from the impression structure of fingerprint pattern 401 and the scanning frequency for the sensing.

Figure 5C:
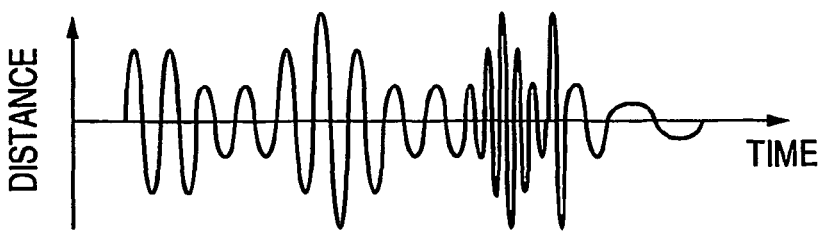
Figure 5D:
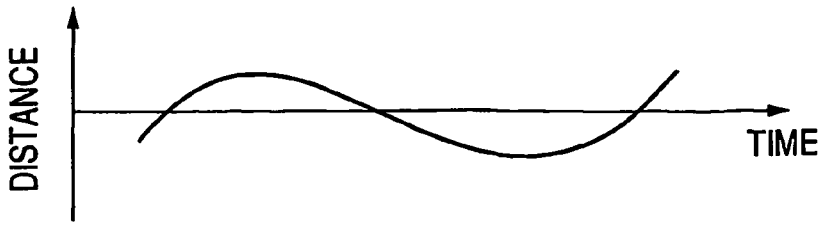

As described above, the synthesized waveform derived from the distance relation between a scanning point of the terahertz wave on the fingertip and electromagnetic wave-detecting section 101 is considered to be superposition of the information on fingerprint impression shape and the information on the state of the pulse vibration. The signal component for the fingerprint impression is controllable by the scanning frequency, and the vibration component of the pulse in the fingertip is a relatively regular signal component of from tens to hundreds of hertzes. Therefore, the two kinds of the information are simply separable by filtering or a like arithmetic processing. For example, by filtering the above synthesized waveform for the frequency band of the fingerprint A, information can be obtained, in time series as shown in FIG. 5C, on the changes of the distance (corresponding to the information on the distance between the scanning point on the fingertip and the electromagnetic wave-detecting section 101, namely corresponding to the depth of the depression of the fingerprint pattern) and on the information on rise-depression of the fingerprint (corresponding to the intervals in the fingerprint pattern). The calculation result is introduced to identifying section 104. On the other hand, information on pulse vibration in the fingertip can be obtained as shown in FIG. 5D by extracting, from the synthesized waveform obtained from the fingerprint pattern and the pulse vibration as shown in FIG. 5B, the signal component which is periodical and has a lower frequency corresponding to the pulse vibration transmitted to the fingertip. This information on the pulse vibration is also inputted to identifying section 104.

Identifying section 104 may conduct a step for reconstructing the information on the fingerprint pattern impression arranged in time series, corresponding to the scanning route to obtain image information of the fingerprint pattern.

In this Example, as described above, fingerprint information is derived as a characteristic pattern inherent to a living body, and for improving the real-time detectableness of information of the fingerprint, the information on pulse vibration is derived from the electromagnetic information detected by electromagnetic wave-detecting section 101.

Identifying section 104 identifies the individual person by comparing the derived biological information with the reference signal memorized in biological information-memorizing section 103.

In this Example, the fingerprint pattern on the fingertip and pulse vibration transmitted to the fingertip are utilized in combination as the plural kinds of biological information, but the combination is not limited thereto. The information for the combination includes temperature at or around the fingertip, an impedance change, a water content, and a fingertip tissue. The number of the kinds of combined biological information is not limited to two.

The electromagnetic wave employed in the present invention has a certain resolving power, a rectilinear propagation property like light, and penetrability as the electromagnetic wave. Therefore, the fingerprint identifying apparatus may be of a noncontact type, being different from conventional contact type ones.

As shown in this Example, combination of fingertip pulse information detection to a fingerprint identification apparatus improves real-time detectableness in the identification, thereby preventing effectively preparation of an imitated fingerprint or direct cutting out of a fingerprint for pretension to be the subject person, being different from a conventional method. This method will improve the security in identification.

The fingerprint identification apparatus is capable of identifying an individual person without contact with the person, and utilizes electromagnetic wave which is somewhat penetrative. Therefore, the fingerprint identification apparatus may be housed in a casing. For example, an easy-handleable identification apparatus can be produced which identifies an individual person automatically without giving a stress to the identified object person, for example, by simple touch with a keyboard or power switch of a personal computer.

Example 3

Retina Identification

This Example shows an application of an identification apparatus of the present invention to identification of an individual person by combination of a personal characteristic pattern with biological information of the person. A retina identification apparatus is used in this Example. The retina identification apparatus renders unnecessary the ID card or password which is essential in log-in to an ATM, a personal computer, or the like.

Figure 6:
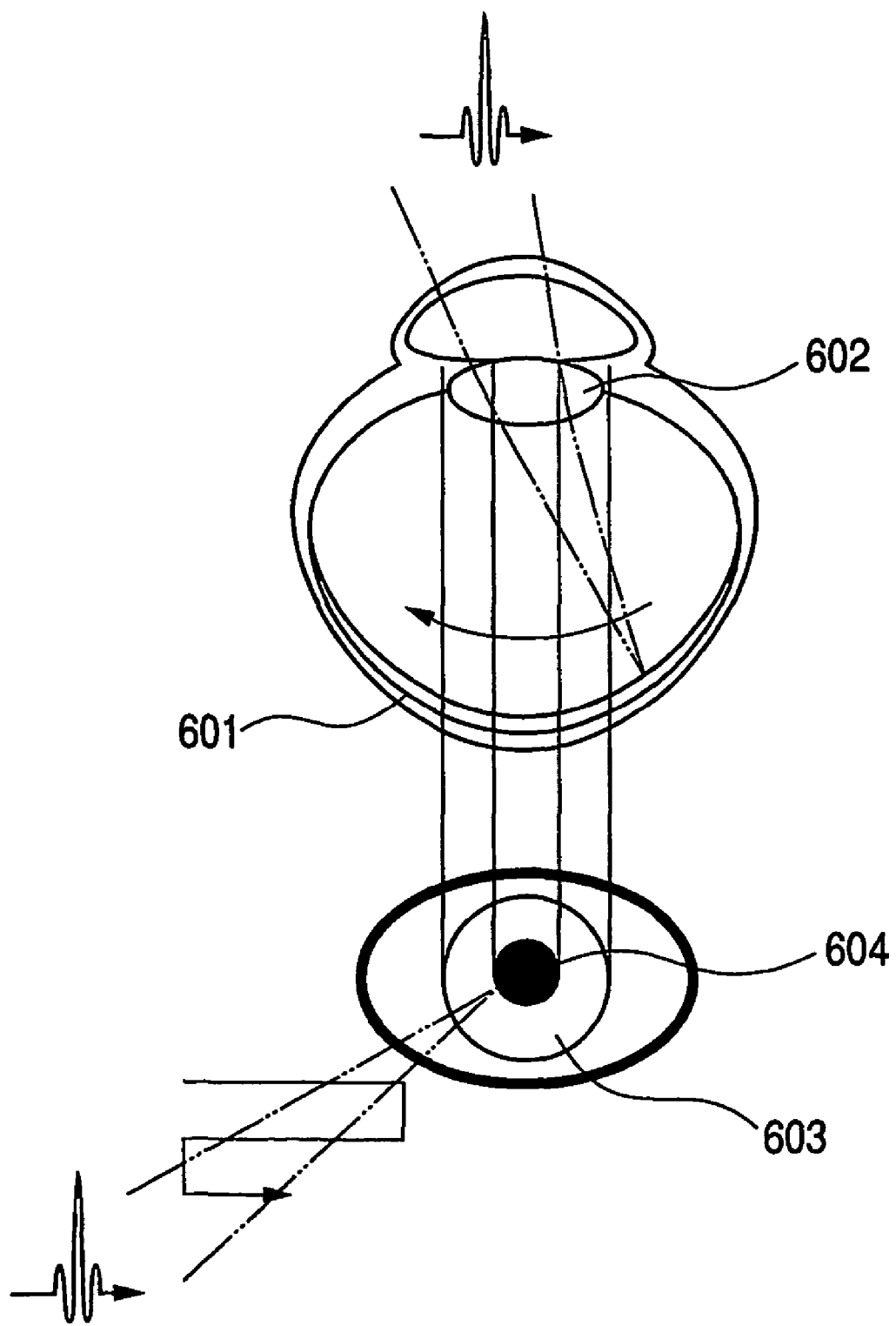
FIG. 6 is a drawing for explaining the retina identification apparatus of Example 3.

The retina identification apparatus of this Example has a constitution as shown in FIG. 1. An impulse wave of a pulse width of about 10 psec is employed as the electromagnetic wave. The retina pattern and eye lens shape of a person are utilized as the biological information in this Example as shown in FIG. 6. FIG. 6 contains a sectional view and a front view of a human eyeball. In FIG. 6, retina 601 is an inside wall of the eyeball, functioning like a film of a camera. In this Example, the term a "retina pattern" signifies a pattern of a blood vessel on retina 601. Eye lens 602 functions like a lens of a camera and adjusts the focus by adjusting the thickness of eye lens 602. Iris 603 has a hole called a pupil 604 at the center. Iris 603 and pupil 604 function like an aperture of a camera and adjust the quantity of light entering the eye. Iris 603 has a pattern (generally called an iris pattern) characteristic to an individual person, being utilized frequently for identification of the person.

In this Example, the terahertz wave projected from electromagnetic wave-detecting section 101 is introduced through eye lens 602 to retina 601, reflected by this retina 601 back to electromagnetic wave-detecting section 101. In this process the terahertz wave projected from electromagnetic wave-detecting section 101 is focused on a fine spot in the region of the retina pattern on retina 601, and the focused spot is allowed to scan the region successively. The method for scanning the retina 601 is not limited to the above method. Otherwise the scanning may be conducted by use of plural electromagnetic wave-detecting sections for collective scanning of a part of retina 601 or the entire region of the retina pattern, or may be conducted by moving the eyeball. The reflected terahertz wave detected by electromagnetic wave-detecting section 101 contains information on a retina pattern obtained from difference of a blood vessel pattern on retina 601 from other living tissues, and additional information in superposition on terahertz wave absorption/reflection characteristics obtained from the thickness shape B of the eye lens existing in the transmission route of the terahertz wave as variation of the terahertz wave reaching electromagnetic wave-detecting section 101.

In this Example, electromagnetic wave-detecting section 101 focuses the terahertz wave on retina 601; allows the focused spot to scan the region of retina pattern A successively to measure absorption/reflection characteristics of the terahertz wave at the scanned spots; and outputs the measurement results to biological information-collecting section 102. The terahertz wave covers various absorption wavelengths of living tissues, having different transmission characteristics for the respective living tissues. Therefore, the information on the blood vessel pattern (retina pattern) on retina 601 can be obtained by detecting the difference in the transmission characteristics. Further, in the terahertz wave transmission path, eye lens 602, for Example, exists. Naturally, the eye lens 602 affects the transmission characteristics of the terahertz. The eye lens 602 incessantly changes its thickness for focusing. This thickness change is considered to change incessantly the terahertz wave transmission path in eye lens 602. Therefore, the intensity information of the terahertz introduced to biological information-collecting section 102 contains also the intensity change information caused by the thickness change of eye lens 602 in addition to the information on the living tissue of retina 602.

Figure 7A:
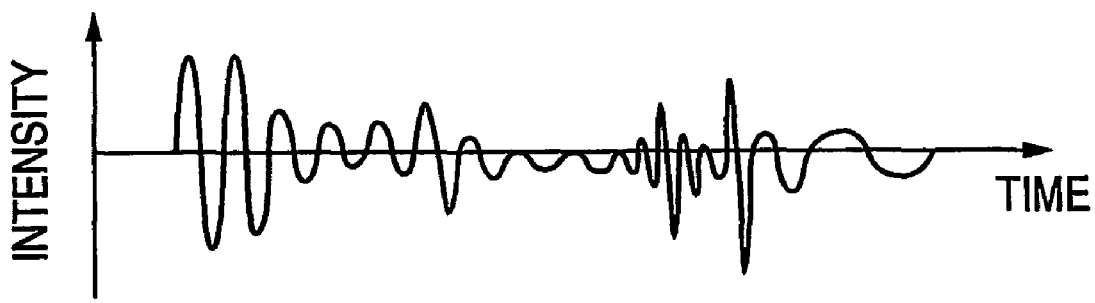
FIGS. 7A, 7B and 7C are drawings for explaining the operation in Example 3.

In this Example, electromagnetic wave-detecting section 101 projects a terahertz wave onto retina 602. The intensity of the reflected terahertz wave from the scanning spot on retina 601 is changed by the difference in the living tissues (difference between the blood vessel pattern and other living tissue) in the retina pattern, and transmission path length of the terahertz wave caused by the thickness change of eye lens 602. Biological information-collecting section 102 detects the response of these terahertz waves in time series to obtain a synthesized oscillation waveform which is composed of a vibration waveform of the retina pattern corresponding to difference in the living tissue of the retina (the shape of the retina pattern on the scanning line of the focused terahertz wave) and a response waveform corresponding to the shape of eye lens 602 as shown in FIG. 7A. The frequency of the obtained response waveform corresponding to the retina pattern (signal of high frequency component in FIG. 7A) is controlled by the scanning frequency of the scanning spot by the focused terahertz wave.

Figure 7B:
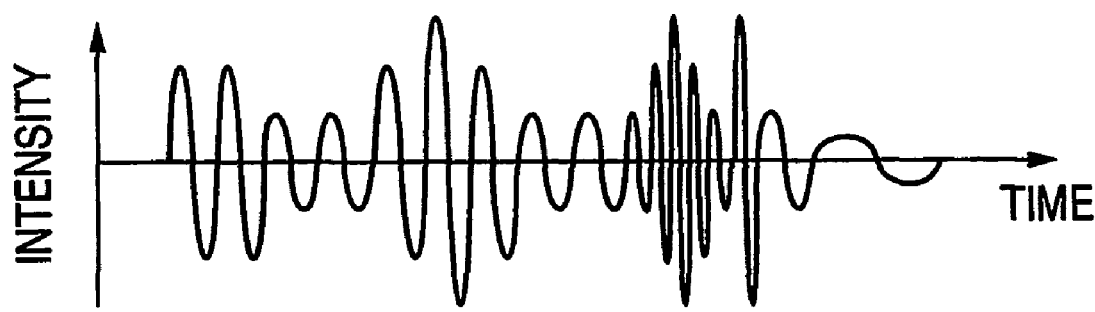
Figure 7C:
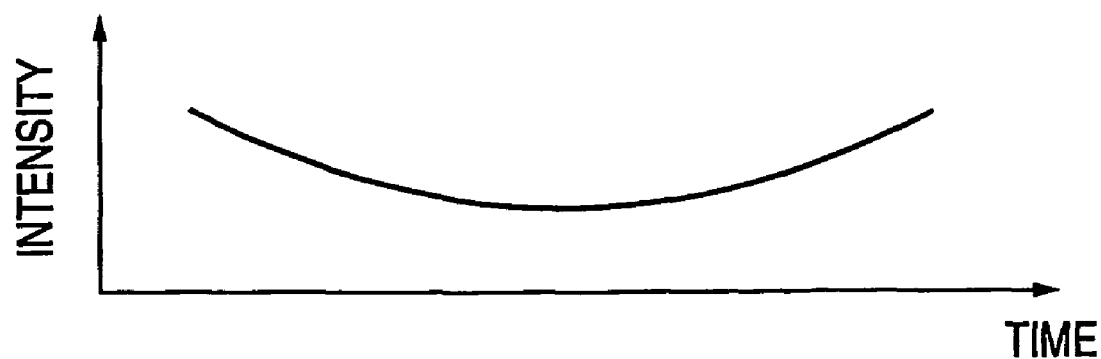

As described above, the synthesized waveform obtained from the change of transmission state caused by the living tissue in the transmission path of the terahertz wave is considered to be formed by superposition of the information on the retina pattern on retina 601 and the information on the thickness shape of eye lens 602. The signal component corresponding to the retina pattern is controllable by the scanning frequency, and the signal component corresponding to the thickness change of focusing of eye lens 602 is readily separable by arithmetic processing like filtering since this component distributes in a low frequency region. For Example, by filtering this synthesized waveform for the frequency region of the retina pattern, a signal can be obtained which shows the change of the intensity (corresponding to the difference between the living tissues on retina 601) and of the frequency (corresponding to intervals of the retina) in time series as shown in FIG. 7B. This calculation result is outputted to identifying section 104. On the other hand, a signal component corresponding to the thickness shape of eye lens 602 as shown in FIG. 7C is obtained by extracting the signal component in the low frequency region from the synthesized waveform shown in FIG. 7A. This calculation result is also outputted to identifying section 104. In this Example, a larger thickness of the eye lens gives a smaller signal intensity of the obtained electromagnetic wave. However, with a certain signal processing method, a smaller thickness of the eye lens gives a smaller signal intensity of the obtained electromagnetic wave.

Identifying section 104 may contain a step of reconstructing the time-series information of the retina pattern according to the scanning route to obtain information on the image of the retina pattern.

The focusing point of the eye can be changed by changing the position of electromagnetic wave-detecting section 101 relative to the eyeball. The focusing point of the eye caused change of the shape of the eye lens, more specifically change of thickness of the eye lens. The information on this movement for the shape change can be outputted as the biological information to identifying section 104.

As described above in this Example, retina information is obtained as a characteristic pattern inherent to a living body, and for improvement of real-time detectableness of the retina information, information on the shape of the eyeball or on movement for changing shape B of the eyeball is obtained from electromagnetic wave information detected by electromagnetic wave-detecting section 101.

Identifying section 104 compares the biological information with a reference signal of living body memorized in biological information-memorizing section 103 to identify the individual person from the relation between the information and the reference signal.

As the plural kinds of biological information, a retina pattern of an eyeball, and a shape of an eye lens or movement for shape change of the eye lens are utilized in combination in this Example. However, the combination is not limited thereto. For example, the information to be combined includes information on an iris; contraction or dilation of a pupil; temperature information, impedance change, water content around an eyeball; movement of an eyeball itself. The number of the kinds of combined biological information is not limited to two.

As shown in this Example, combined use of the eye lens information in retina identification improves real-time detectableness in the identification, thereby preventing effectively pretension to be the subject person by collection and imitating a retina pattern, or direct cutting-out of the pattern. This method will improve the security in identification.

The electromagnetic wave used for detection of a retina pattern is less stimulative to the eye than light, and the identification be conducted without damaging the living tissue of the eyeball by abrupt irradiation of high-power light. Thus the present invention provides an identification apparatus highly safe to the human body.

This application claims priority from Japanese Patent Application No. 2004-092398 filed on Mar. 26, 2004, which is hereby incorporated by reference herein.

The invention claimed is:

1. A method of identification of a living body, comprising the steps of:
   a first detecting step of detecting a first electromagnetic wave in a frequency band ranging from 300 GHz to 30 THz reflected from the living body;
   a second detecting step of detecting a second electromagnetic wave in the frequency band reflected from the living body,
   wherein the first and second electromagnetic waves include superposed biological information;
   a deriving step of deriving a time waveform by using the first and second electromagnetic waves;
   an extracting step of extracting the biological information by filtering the time waveform through a frequency property; and
   a comparing step of comparing the biological information with preliminarily memorized biological information,
   wherein the biological information extracted from the time waveform is derived from delay times of the first and second electromagnetic waves caused by a change of position in time of a portion of the living body.

2. The method of identification according to claim 1, wherein the biological information is information on positional variation selected from the group consisting of pulse vibration, voice cord variation, bone vibration, shape change of eye lens, pupil contraction and pupil dilation.

3. The method of identification according to claim 1, wherein the biological information is any one selected from the group consisting of a fingerprint, a voiceprint and a retina pattern.

4. A method of identification of a living body, comprising the steps of:
   a first generating step of generating a first electromagnetic wave pulse in a frequency band ranging from 300 GHz to 30 THz;

a first detecting step of detecting the first electromagnetic wave pulse reflected by the living body;

a second generating step of generating a second electromagnetic wave pulse in the frequency band;

a second detecting step of detecting the second electromagnetic wave pulse reflected from the living body, wherein the first and second electromagnetic wave pulses include superposed biological information;

a deriving step of deriving a time waveform by using the first and second electromagnetic wave pulses;

an extracting step of extracting the biological information by filtering the time waveform through a frequency property; and a comparing step of comparing the biological information with preliminarily memorized biological information, wherein the biological information extracted from the time waveform is derived from delay times of the first and second electromagnetic wave pulses caused by a change of position in time of a portion of the living body.

5. An apparatus for identifying a living body, comprising:

a detecting section for detecting first and second electromagnetic wave pulses in a frequency band ranging from 300 GHz to 30 THz reflected from the living body, the first and second electromagnetic wave pulses including superposed biological information;

an information-collecting section for deriving a time waveform by using the first and second electromagnetic wave pulses and extracting the biological information by filtering the time waveform through a frequency property;

a memory section for preliminarily memorizing biological information; and an identifying section for comparing the biological information extracted by the information-collecting section with the biological information memorized by the memory section, wherein the biological information extracted from the time waveform is derived from delay times of the first and second electromagnetic waves caused by a change of position in time of a portion of the living body.

6. An apparatus for identifying a living body, comprising:

a generating section for generating first and second electromagnetic wave pulses in a frequency band ranging from 300 GHz to 30 THz;

a detecting section for detecting the first and second electromagnetic wave pulses reflected by a living body, the first and second electromagnetic wave pulses including superposed biological information;

an information-collecting section for deriving a time waveform by using the first and second electromagnetic wave pulses and extracting the biological information by filtering the time waveform through a frequency property;

a memory section for preliminarily memorizing biological information; and an identifying section for comparing the biological information extracted by the information-collecting section with the biological information memorized by the memory section, wherein the biological information extracted from the time waveform is derived from delay times of the electromagnetic wave caused by a change of position in time of a portion of the living body.

7. The apparatus according to claim 6, wherein the information-collecting section derives the time waveform regarding the biological information, the memory section preliminarily memorizes a time waveform regarding the living body, and the identifying section compares the time waveform regarding the living body derived by the information-collecting section with the time waveform regarding the living body memorized by the memory section to identify the living body.

8. A method of identification of a living body, comprising the steps of:

a first generating step of generating a first electromagnetic wave pulse in a frequency band ranging from 300 GHz to 30 THz;

a first detecting step of detecting the first electromagnetic wave pulse reflected by the living body;

a second generating step of generating a second electromagnetic wave pulse in the frequency band;

a second detecting step of detecting the second electromagnetic wave pulse reflected from the living body, wherein the first and second electromagnetic wave pulses include superposed biological information;

a deriving step of deriving a time waveform by using the first and second electromagnetic wave pulses;

a separating step of separating a time waveform regarding the biological information by filtering the time waveform through a frequency property; and a comparing step of comparing the derived time waveform regarding the biological information with a time waveform regarding preliminarily memorized biological information, wherein the biological information extracted from the time waveform is derived from delay times of the first and second electromagnetic wave pulses caused by a change of position in time of a portion of the living body.

9. The method of identification according to claim 8, further comprising a step of identifying the living body by the result of the comparing step.

10. A method for deriving a time waveform, comprising the steps of:

detecting an electromagnetic wave in a frequency band ranging from 300 GHz to 30 THz reflected from the living body, the electromagnetic wave including superposed biological information; and deriving a time waveform of the electromagnetic wave by sampling the electromagnetic wave detected in the detecting step, wherein the biological information extracted from the time waveform is derived from a delay time of the electromagnetic wave caused by a change of position in time of a portion of the living body.

11. The method of identification according to claim 1, further comprising a step of identifying the living body by the result of the comparing step.

* * * * *